United States Patent [19]
Lee et al.

[11] Patent Number: 5,405,347
[45] Date of Patent: Apr. 11, 1995

[54] ADJUSTABLE CONNECTOR FOR EXTERNAL FIXATION RODS

[75] Inventors: Harry E. Lee; Thomas Russell, both of Memphis, Tenn.; Aniruddha Nazre, Warsaw, Ind.

[73] Assignee: Zimmer, Inc., Warsaw, Ind.

[21] Appl. No.: 16,909

[22] Filed: Feb. 12, 1993

[51] Int. Cl.⁶ ............................................. A61B 17/56
[52] U.S. Cl. ....................................... 606/54; 606/59; 403/53; 403/59; 403/81; 403/103; 403/381
[58] Field of Search .......................... 606/53–59, 606/86, 90, 105; 403/381, 53, 58, 59, 81, 103, 104, 106

[56] References Cited

U.S. PATENT DOCUMENTS

| | | | |
|---|---|---|---|
| 2,333,033 | 10/1943 | Mraz | 606/59 |
| 2,911,178 | 11/1959 | Joffe | 403/381 |
| 3,976,061 | 8/1976 | Volkov et al. | |
| 3,977,397 | 8/1976 | Kalnberz et al. | |
| 4,033,340 | 7/1977 | Kalnberz | |
| 4,185,623 | 1/1980 | Volkov et al. | |
| 4,312,336 | 1/1982 | Danieletto et al. | |
| 4,365,624 | 12/1982 | Jaquet | |
| 4,502,473 | 3/1985 | Harris et al. | |
| 4,615,338 | 10/1986 | Ilizarov et al. | |
| 4,621,627 | 11/1986 | DeBastiani et al. | |
| 4,714,076 | 12/1987 | Comte et al. | |
| 4,768,524 | 9/1988 | Hardy | |
| 4,784,125 | 11/1988 | Monticelli et al. | |
| 4,823,781 | 4/1989 | Buchanan | |
| 4,923,458 | 5/1990 | Fischer | 606/59 |
| 4,936,843 | 6/1990 | Sohngen | 606/54 |
| 4,973,331 | 11/1990 | Pursley et al. | 606/54 |
| 4,988,349 | 1/1991 | Pennig | 606/58 |
| 5,019,077 | 5/1991 | De Bastiani et al. | 606/54 |
| 5,026,372 | 6/1991 | Sturtzkopf | 606/54 |
| 5,041,112 | 8/1991 | Mingozzi et al. | 606/54 |
| 5,062,844 | 11/1991 | Jamison et al. | 606/54 |
| 5,074,866 | 12/1991 | Sherman et al. | 606/56 |
| 5,095,919 | 3/1992 | Monticelli et al. | 606/56 |
| 5,112,331 | 5/1992 | Vel Miletich | 606/53 |
| 5,152,280 | 10/1992 | Danieli | |
| 5,167,661 | 12/1992 | Wagenknecht | 606/54 |

FOREIGN PATENT DOCUMENTS

| | | |
|---|---|---|
| 0261252 | 3/1988 | European Pat. Off. |
| 0420813A1 | 4/1991 | European Pat. Off. |
| 0481697A1 | 10/1991 | European Pat. Off. |
| 0460944A1 | 12/1991 | European Pat. Off. |
| 2517535 | 6/1983 | France .................. 606/57 |
| 2250682A | 6/1992 | United Kingdom . |
| WO92/02184 | 2/1992 | WIPO . |

Primary Examiner—Tamara L. Graysay
Attorney, Agent, or Firm—Todd A. Dawson

[57] ABSTRACT

This invention provides for the angular and lateral adjustment of a pair of fixator rods in an infinite number of planes. The angular adjustment member may be rotated about a center axis of the connector such that the connected fixator rods may be angled relative to one another in any plane called for. Similarly, the lateral adjustment may be rotated about the center axis of the connector such that the two fixator rods may be shifted laterally relative to one another in any direction. The adjustable connector provides for the adjustment of the fixator rods after the rods have been connected to the bone pins. Therefore, after a surgeon has reduced and stabilized the fracture, minor adjustments can be carried out to fully align the bone fragments without disconnecting the fixator rods or the bone pins. After all adjustments have been made, a series of locking bolts or pins can be engaged to hold the adjustable connector in a fixed position.

15 Claims, 6 Drawing Sheets

ADJUSTABLE CONNECTOR FOR EXTERNAL FIXATION RODS

FIELD OF THE INVENTION

This invention relates to external fixators as used in the reduction and stabilization of long bone fractures and has specific relevance to an adjustable link for positioning between a pair of fixation rods.

BACKGROUND OF THE INVENTION

External fixators used for the reduction and stabilization of long bone fractures are well known in the field of orthopaedics. Typically the fixator includes an elongate rod which has a plurality of bone pins connected thereto by a series of clamps. A limitation with prior art fixators occurs when after the fixator and bone pins are connected, the surgeon notes that one of the sections of fractured bone is out of alignment. With prior art fixators which have a single elongate rod to support the bone pins, the surgeon would be required to disconnect some or all of the pins so that the fracture may be re-aligned.

While pivotally linked fixator rods have been developed to minimize the problem, the direction of movement is limited.

SUMMARY OF THE INVENTION

This invention provides for the angular and lateral adjustment of a pair of fixator rods in an infinite direction about the longitudinal axis of the connector. The angular adjustment member may be rotated about a center axis of the connector such that the connected fixator rods may be angled relative to one another in any direction required. Similarly, the lateral adjustment may be rotated about the center axis of the connector such that the two fixator rods may be shifted laterally relative to one another in any direction. The adjustable connector provides for the adjustment of the fixator rods after the rods have been connected to the bone pins without disassembling the fixator setup. Therefore, after a surgeon has reduced and stabilized the fracture, minor adjustments can be carried out to fully align the bone fragments without disconnecting the fixator rods or the bone pins. After all adjustments have been made, a series of set screws are tightened to maintain the adjustable connector in a fixed position.

Accordingly, it is an advantage of the invention to provide for a novel adjustable connector for a pair of external fixator rods which provides for the angular and lateral adjustment of the rods relative to one another.

Another advantage of the invention is to provide for an adjustable connector for a pair of fixator rods wherein the angular adjustment mechanism may be rotated about a longitudinal axis of the connector.

Another advantage of the invention is the ability to rotate a lateral adjustment mechanism about the longitudinal axis of the body such that a pair of fixator rods connected to the body may be laterally shifted in any direction.

Another advantage of the invention is to provide for a connector for a pair of external fixator rods which can be adjusted after the fixator rods are connected to bone pins.

Other advantages of the invention will become apparent upon a reading of the following description taken with the accompanying drawings.

DESCRIPTION OF THE PREFERRED EMBODIMENT

The preferred embodiment herein described is not intended to be exhaustive or to limit the invention to the precise form disclosed. Rather, it is chosen and described to best explain the invention so that others skilled in the art might utilize its teachings.

For simplicity, the following description of the adjustable connector of the invention is divided into a section discussing the lateral adjustment mechanism and a section discussing the angular adjustment mechanism. It is to be understood that although described as separate components, the two combine to yield a connector which can be angularly and laterally adjustable after connection.

LATERAL ADJUSTMENT MECHANISM

Figure 1:
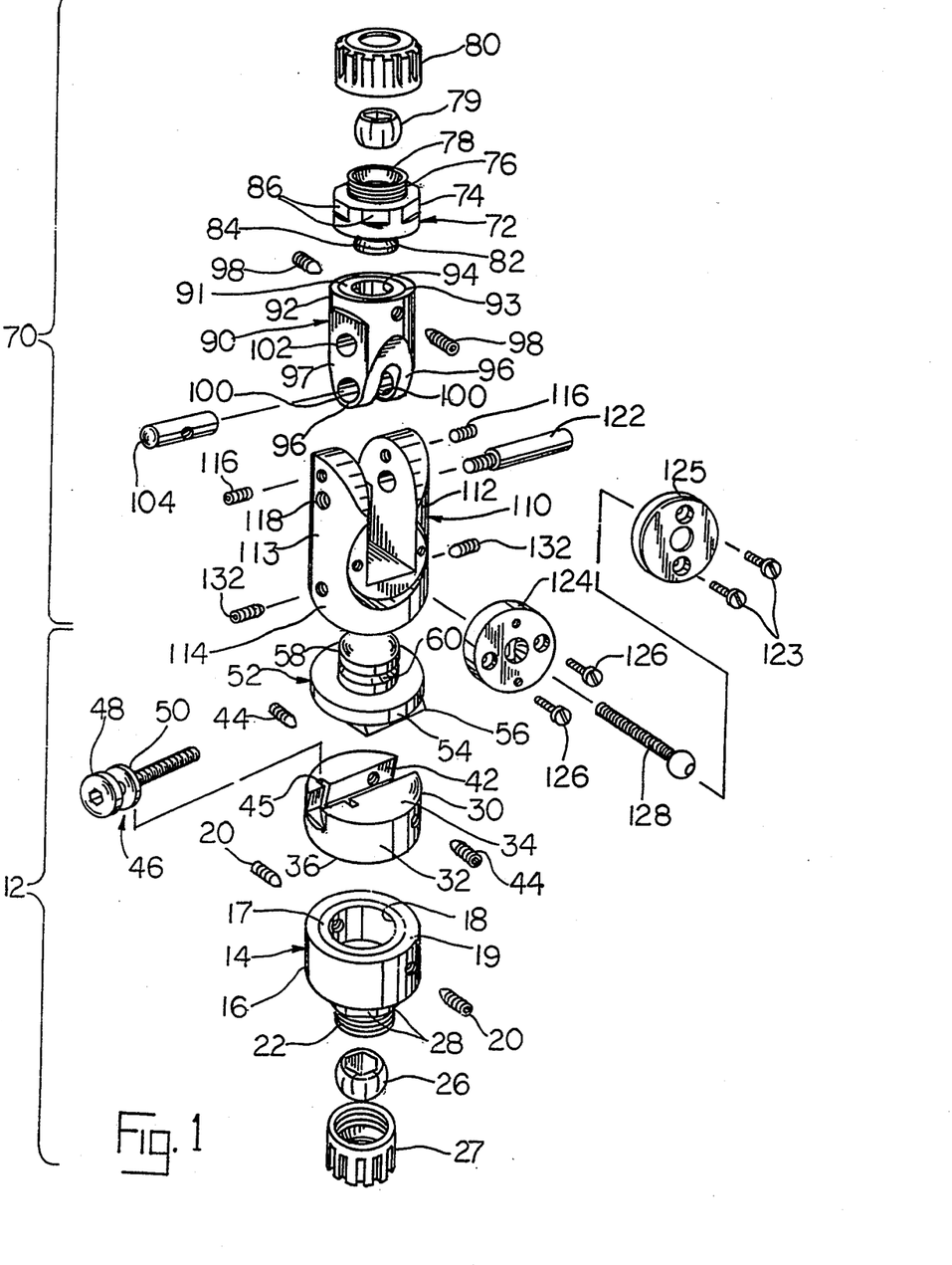
FIG. 1 is an exploded perspective view of the adjustable connector of the invention.
Figure 2:
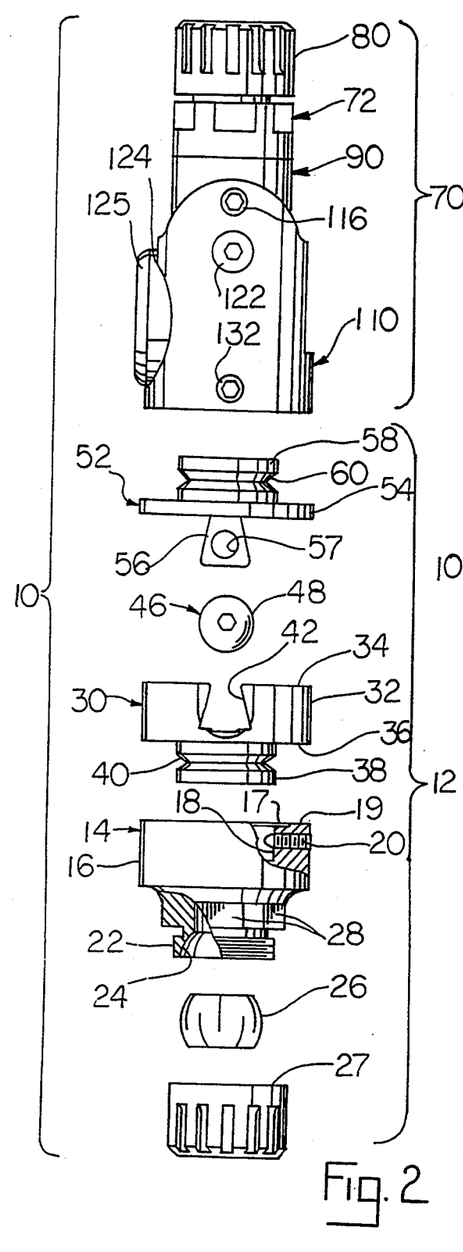
FIG. 2 is an elevational view of the adjustable connector with the lateral adjustment section exploded for illustrative purposes.

Referring to FIGS. 1 and 2, the adjustable connector 10 is illustrated with the lateral adjustment mechanism 12 exploded to reveal the component parts. Lateral adjustment mechanism 12 includes a base 14 which includes a generally cylindrical portion 16 defining an interior cavity 18. Base 14 terminates in an upper surface 19 having an annular flat groove 17 adjacent cavity 18. A pair of threaded bores are provided within base 14 in communication with cavity 18 for accommodating set screws 20 such that screws 20 can extend into cavity 18. An externally threaded throat 22 extends longitudinally from portion 16 of base 14 and defines a cavity 24 shaped as illustrated. Cavity 24 accommodates a spherical slotted connection device 26 and a portion of an external fixation rod (see FIGS. 8 and 9). An end cap 27 screws onto throat 22 to compress the slotted connection device 26 for clamping engagement with the fixator rod, A series of flats 28 are formed on base 14 between the throat 22 and portion 16 to provide a surface for connection of a tightening device such as a wrench (not shown). Base 14 is fixed relative to the fixation rod (FIGS. 8 and 9) after the end cap 27 compresses the connection device 26 onto the fixator rod.

An intermediate component 30 is provided and as is illustrated includes a plate 32 having a circular periphery defining an upper surface 34 and a lower surface 36.

A generally cylindrical post 38 having a circumference substantially conforming to cavity 18 extends integrally from lower surface 36 and includes an annular V-shaped groove 40. A dovetail shaped slot 42 is formed in plate 32 extending into the plate from upper surface 34 as illustrated. A longitudinal groove 35 is formed centrally on the bottom wall of the dovetail slot 42. A pair of threaded bores are formed in the peripheral side wall of plate 32 and are in communication with slot 42. A pair of set screws 44 are accommodated by the threaded bores for extension into the dovetail slot 42. A slot 45 is formed in plate 32 transverse to slot 42 and adjacent one end thereof. A screw 46 is positioned within slot 42 and includes a head 48 and a collar 50 spaced from the head as illustrated. Collar 50 is accommodated within slot 45 and rotates freely therein about the longitudinal axis of the screw 46. Intermediate component 30 is configured for connection to base 14. Cylindrical post 38 is seated within cavity 18 of base 14 with the upper surface 19 and lower surface 36 in abutting engagement. Intermediate component 30 is rotatable relative to base 14 about post 38. Intermediate component 30 may be held fixed relative to base 14 by turning screws 20 into their threaded bores such that the pointed end of the screws contact the V-shaped groove of the post in an interference fashion. Groove 17 reduces the surface contact between base 14 and intermediate component 30 thereby reducing the friction between the two components making the rotation of component 30 relative to component 14 easier.

Figure 11:
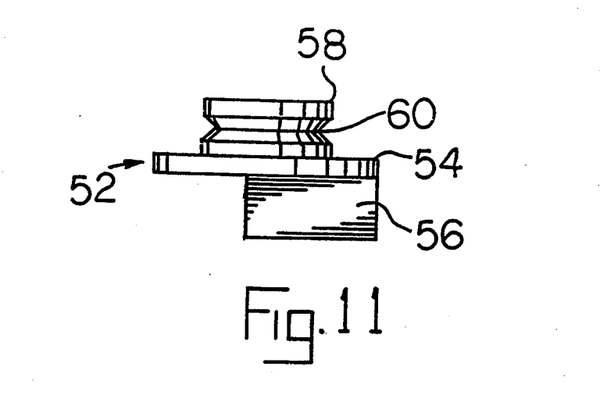
FIG. 11 is an elevational view of upper component 52.

An upper component 52 for connection between the intermediate component 30 and angle adjustment mechanism 70 (described below) is provided and includes a plate 54 having a circular periphery closely matching the periphery of intermediate component 30. A dovetail shaped rail 56 extends along one surface of plate 54 and is slidably accommodated within the dovetail shaped slot 42 of the intermediate plate 30. Rail 56 extends a partial distance across the diameter of plate 54 and includes a threaded central longitudinal bore 57 for accommodating the shaft of screw 46 carried by the intermediate plate 30. A cylindrical post 58 similar to post 38 extends integrally from plate 54 on an opposite side of rail 56. Post 58 includes an annular V-shaped groove 60.

ANGULAR ADJUSTMENT MECHANISM

Figure 3:
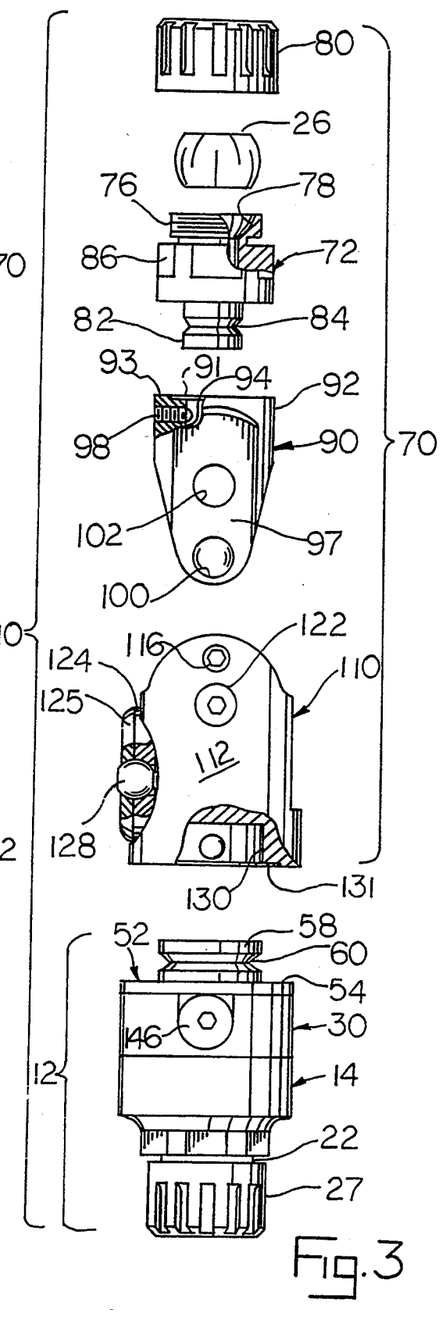
FIG. 3 is an elevational view of the adjustable connector with the angular adjustment mechanism exploded for illustrative purposes.
Figures 4, 5:
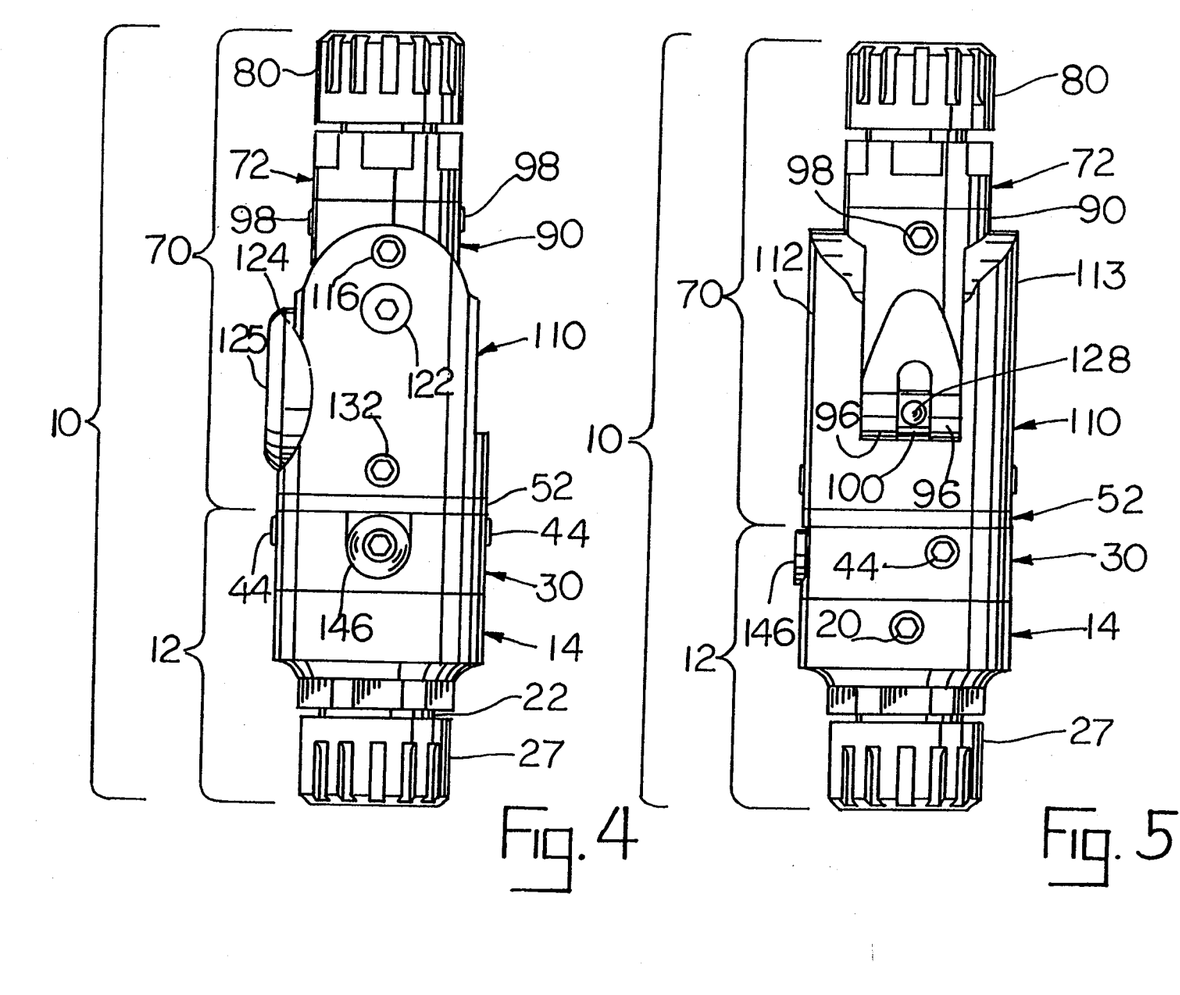
FIGS. 4–7 are side elevational view of the adjustable connector of the invention.
Figures 6, 7:
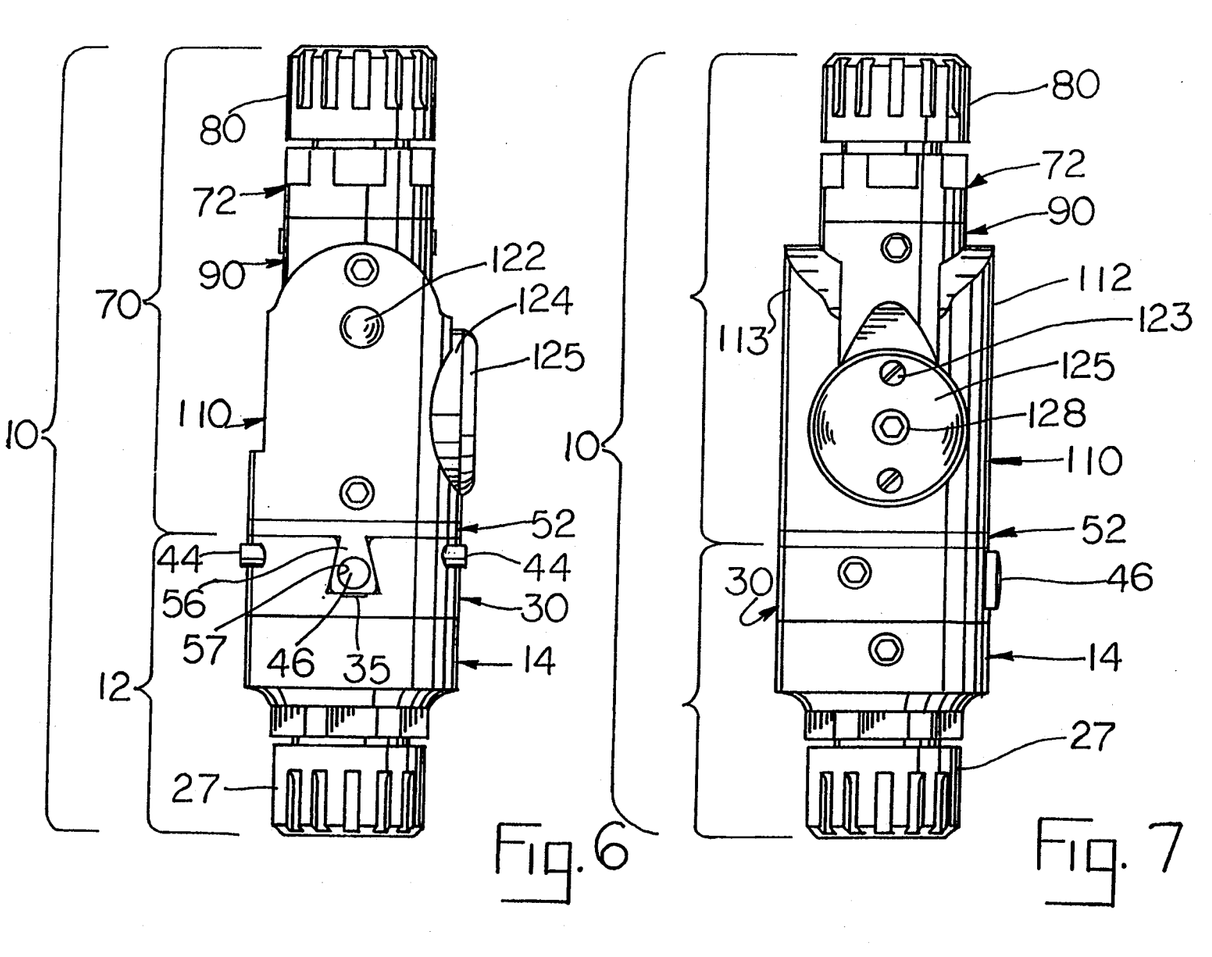

Angular adjustment mechanism 70 is shown in exploded view in FIGS. 1 and 3 and includes a base 72 which includes a plate 74 having a circular periphery. An externally threaded throat 76 extends from one side of plate 74 and includes a cavity 78 which is substantially similar to the cavity 24 of base 14 for the accommodation of a clamping device 79 and an end portion of a fixator rod. Cap 80 screws onto throat 76 for compressing the clamping device about the fixator rod to secure the rod to the angular adjustment mechanism 70. A generally cylindrical post 82 extends from plate 74 opposite throat 76 and includes a annular V-shaped grove 84. A plurality of flats 86 are formed about the periphery of plate 74 for accommodation of a tightening device such as a wrench (not shown).

An intermediate component 90 is provided and includes a body 92 having a cylindrical end with a cylindrical cavity 94 formed therein. An annular groove 91 is formed on the upper surface 93 about cavity 94. The opposite end of body 92 is forked and includes a pair of legs 96 which terminate in an arcuate tapered ends as illustrated. A flattened outer surface 97 is formed on each leg 96. Legs 96 are spaced from one another to define an opening therebetween as illustrated in the figures. A smooth through bore 100 is formed in each leg 96 adjacent its arcuate end. A through bore 102 is formed through body 92 parallel with through bores 100. A pair of threaded bores are formed in the cylindrical end of body 94 in communication with cavity 94 for accommodation of set screws 98. A smooth shaft 104 is carried within through bores 100 and rotates freely therein. Shaft 104 includes a central transverse through bore 106 having internal threads. Bore 106 is in alignment with the opening between legs 96.

A lower component 110 is provided and includes a pair of spaced legs 112, 113 extending integrally from a circular plate 114 and each having an arcuate periphery and terminating in an arcuate end as illustrated in the figures. A threaded bore is formed adjacent the distal ends of legs 112, 113 for accommodating set screws 116 therein. A second threaded bore 118 is formed in leg 113 as illustrated. A smooth throughbore 120 is formed in leg 112 in alignment with threaded bore 118. Legs 112, 113 are spaced so as to accommodate intermediate component 90 therebetween as illustrated. A pin 122 having a threaded end is inserted through smooth throughbore 120, throughbore 102 and turned within threaded bore 118 to secure the intermediate component 90 to lower component. Intermediate component 90 is rotatable relative to lower component 110 about pin 122. A plate 124 having a central opening is connected by screws 126 to component 110 and spans legs 112, 113. The shaft of screw 128 extends through the central opening of plate 124. A face plate 125 is connected to plate 124 by screws 123 and includes an opening aligned with the central opening of plate 124. The head of screw 128 is generally round and is rotatably captured between plates 124 and 125. The threaded shaft of screw 128 is threadibly accommodated within the central transverse opening of shaft 104 such that as screw 128 is rotated, shaft 104 travels along the screw which causes the intermediate component 90 to rotate about pin 122. A cavity 130 is formed in plate 114 of lower component 110 as illustrated to accommodate the cylindrical component 58 of the lateral adjustment mechanism 12. An annular groove 131 is formed adjacent cavity 130 on the lower surface of component 110. A pair of threaded through bores are formed through plate 114 in communication with cavity 130 for accommodating set screws 132.

In the explanation that follows on the function of the adjustable connector and its various components, it will be assumed that all set screws 20, 44, 98, 116 and 132 are loose and not in compressive engagement with components 38, 56, 82, 90 and 58 respectively. Further, it will be understood that a fixator rod is clamped to bases 14 and 72 by clamping devices 26 and 79 as previously described. Finally, it should be understood that the fixator rods are connected to a bone pin extending into fragmented section of a bone.

Figure 8:
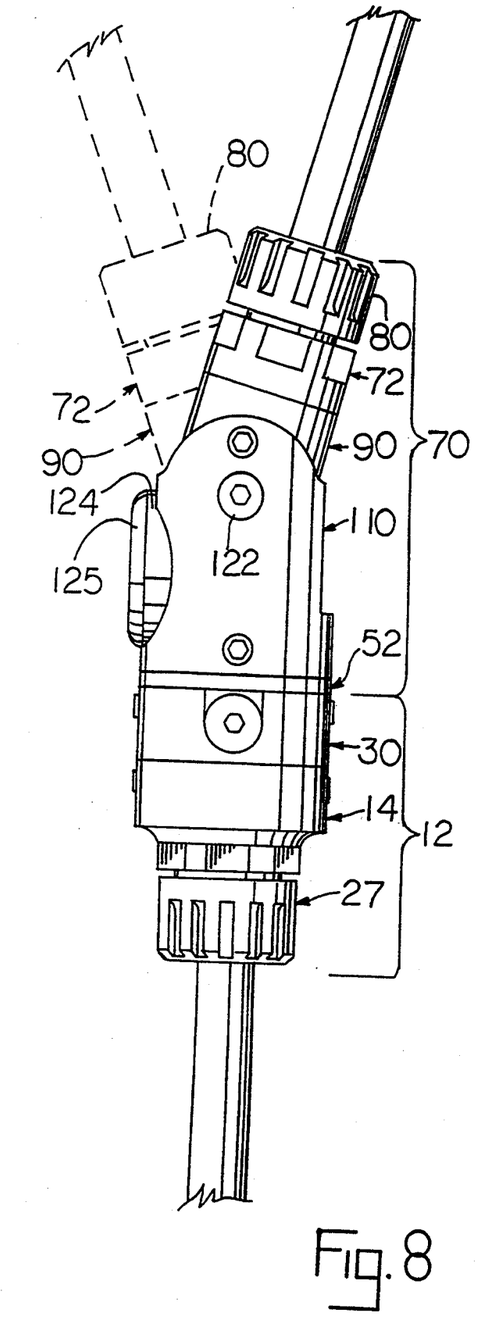
FIG. 8 is an elevational view of the adjustable connector of the invention illustrating the pivotal relationship of the angular adjustment mechanism.
Figure 9:
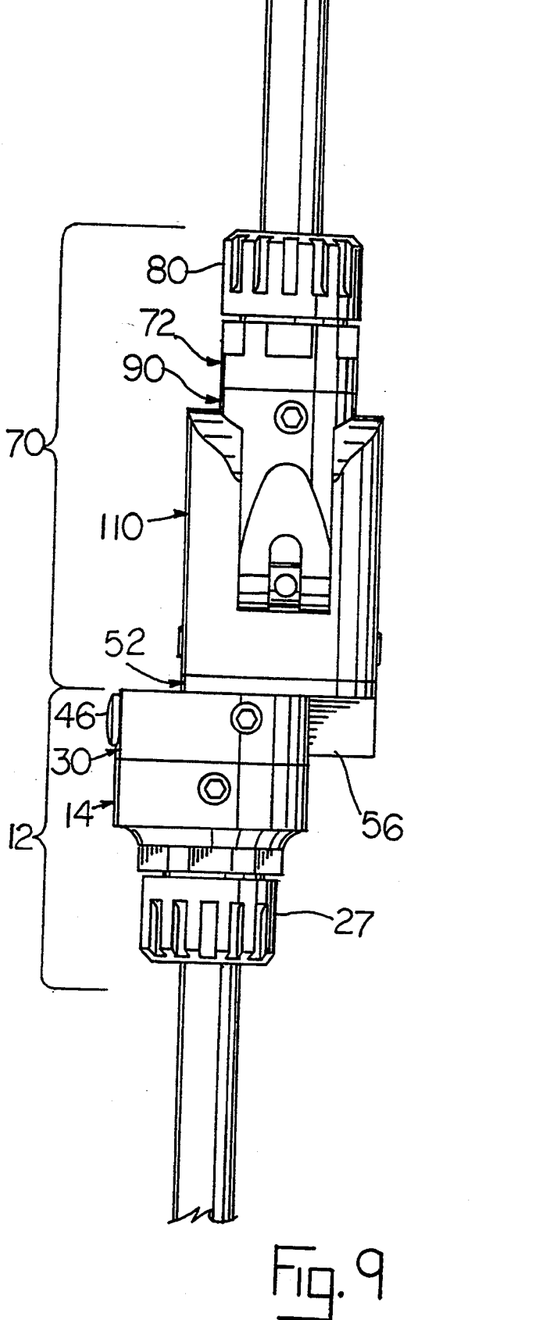
FIG. 9 is an elevational view of the adjustable connector of the invention illustrating the lateral shifting available by use of the lateral adjustment mechanism.

Two basic adjustments are possible using the adjustable connector of the invention, a lateral adjustment as illustrated in FIG. 9 wherein the two fixator rods are laterally offset from one another, and an angular adjustment as illustrated in FIG. 8 wherein the fixator rods are positioned at an angle less than 180 degrees relative to one another. Due to the use of cylindrical posts 38, 58, and 84, the lateral adjustment mechanism 12 and the angular adjustment mechanism 70 may be independently rotated about the cylindrical posts so as to enable the user to effect the lateral and angular adjustments in any direction around the central longitudinal axis of the connector as identified in FIGS. 6 through 9.

Figure 10:
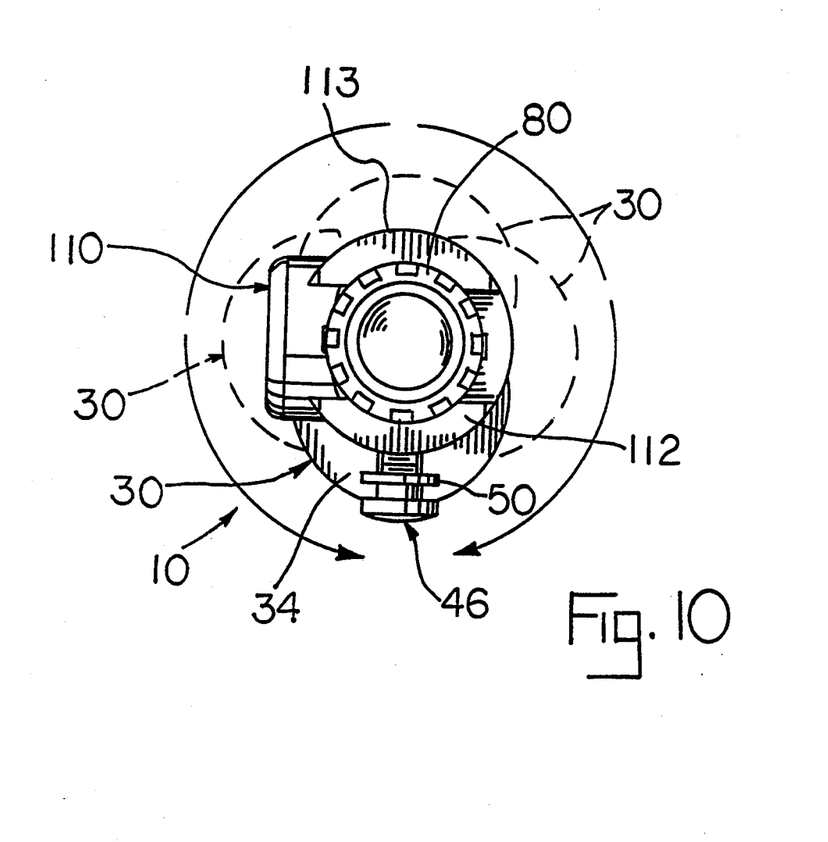
FIG. 10 is an elevational view of the adjustable connector of the invention viewed along its longitudinal axis and illustrating the lateral adjustment capability of the connector.

To adjust the lateral position of the fixator rods, the user inserts a driver, such as a hex wrench, into the head of screw 46 and turns the screw. Rotation of the screw within the threaded bore 57 of dovetail rail 56 causes upper component 52 of the lateral adjustment mechanism 12 to travel within the dovetail slot 42. Groove 35 formed in the dovetail slot 42 reduces the amount of surface contact between intermediate component 30 and the dovetail rail 56 to thereby reduce sliding friction. FIG. 9 illustrates a possible orientation of the upper component 52 relative to intermediate component 30 which can be achieved by rotation of screw 46. Further, since the intermediate component 30 and the upper component 52 are connected to the remaining components by cylindrical posts 38 and 58, components 30 and 52 may be rotated by the surgeon 360 degrees around the longitudinal axis of the mechanism 10. By connecting components 30 and 52 in such a manner, the mechanism provides lateral adjustment of a pair of fixator rods in any direction with a single adjustment mechanism. The rotation freedom of the adjustment mechanism 10 of the invention is illustrated in FIG. 10.

To angle the connected fixator rods relative to one another, the user rotates screw 128 with an appropriate driver instrument (not shown) such as a hex driver. Since the screw head is captured between plates 124 and 125, the screw is laterally static during rotation. However, as screw 128 is rotated, shaft 104 travels along the threaded screw shaft causing intermediate component 90 to rotate about pin 122 as illustrated in FIG. 8. Since intermediate component 90 and lower component 110 are connected to base 72 and the lateral adjustment mechanism 12 by posts 82 and 58 respectively, the intermediate component and the lower component may be rotated 360 degrees on the posts. The ability to rotate these components allows a user to rotate intermediate component 90 in any direction to properly position the attached fixator rods.

It should be well understood that due to the number of posts implemented in the design of this invention, the lateral adjustment mechanism 12 and angle adjustment mechanism 70 may be rotated independently of one another. If desired, by tightening screws 132 into engagement with post 58, the adjustment mechanism 12 and 70 could be rotated together about posts 38 and 82.

Once the user has properly adjusted the lateral adjustment mechanism 12 and the angular adjustment mechanism 70, set screws 20, 44, 132, 116, and 98 may be tightened to rigidly secure the component parts of the device 10 in the desired orientation.

It should be understood that the invention is not to be limited to the precise forms disclosed but may be modified within the keeping of the appended claims.

We claim:

1. An adjustable connector configured for connection to an external fixator rod defining a longitudinal axis, the adjustable connector comprising a lateral adjustment means for laterally shifting said external fixator rod in a direction generally perpendicular to the longitudinal axis, and an angular adjustment means for angularly shifting the external fixator rod relative to the longitudinal axis, wherein the lateral adjustment means includes a first member having a slot formed therein and a second member having a rail substantially conforming to the slot, the rail being slidably accommodated by the slot of the first member wherein said second member may be laterally displaced relative to said first member.

2. The adjustable connector of claim 1 including post means for rotatably connecting the angular adjustment means to the lateral adjustment means such that the angular adjustment means is rotatable about the longitudinal axis independently of the lateral adjustment means.

3. The adjustable connector of claim 1 further including a threaded longitudinal bore formed in the rail and a screw carried by the first member, wherein rotation of the screw causes the second member to shift laterally along the first member relative to the axis.

4. The adjustable connector of claim 1 wherein the angular adjustment means includes a first member rotatably connected to a second member about a pin member, a screw carried by the second member and by an end of the first member wherein rotation of the screw causes the end of the first member to travel along the screw thereby causing said first member to be positioned at an angle relative to said second member.

5. The adjustable connector of claim 1 including connection means configured for connecting the adjustable connector between a pair of fixator rods.

6. The adjustable connector of claim 5 wherein the connection means includes ball members frictionally connected to the fixator rods and to the adjustable connector such that the adjustable connector is rotatable about the longitudinal axis relative to the fixator rods.

7. An adjustable connector configured for connection between a first fixator rod and a second fixator rod, the adjustable connector defining an axis and including a lateral adjustment means for laterally shifting the fixator rods and an angular adjustment means for placing the fixator rods at an angle relative to one another, the lateral adjustment means and the angular adjustment means being interconnected, first clamp means connected to the lateral adjustment means for connecting the lateral adjustment means to the first fixator rod, second clamp means connected to the angular adjustment means for connecting the lateral adjustment means to the second fixator rod.

8. The adjustable connector of claim 7 further including connection means for rotatably connecting the lateral adjustment means and the angular adjustment means together such that the lateral adjustment means and the angular adjustment means are rotatable about the axis.

9. The adjustable connector of claim 7 wherein said first clamp means includes post means for rotatably connecting the first clamp means to the lateral adjustment means and the second clamp means includes post means for rotatably connecting the second clamp means to the angular adjustment means.

10. The adjustable connector of claim 7 wherein the lateral adjustment means includes a base connected to said first clamp means and static relative to the first fixator rod, an intermediate component carried by the base and being rotatable relative to the base, an upper component carried by the intermediate component, and lateral shifting means operatively associated with the intermediate component and upper component for laterally shifting the intermediate component and upper component relative to one another.

11. The adjustable connector of claim 10 wherein the intermediate component includes a slot and the upper component includes a protrusion for slidable accommodation with the slot, said lateral shifting means comprising a screw carried by the intermediate component and secured against lateral movement relative thereto, the screw being threadibly accommodated within the protrusion such that as the screw is rotated, the protrusion and upper component travels along the screw to laterally shift the upper component relative to the intermediate component and the base.

12. The adjustable connector of claim 11 including set screws carried by the intermediate component for selectively engaging the protrusion on the upper component to secure the upper component against further lateral shifting relative to the intermediate component.

13. The adjustable connector of claim 7 wherein the angular adjustment means includes a base for connection to the second fixator rod, an intermediate component for connection to the base being rotatable relative thereto around an axis of the base and a lower component connected to the lateral adjustment means and being rotatable relative thereto about the axis of the adjustable connector, the lower component including a pair of space legs, a portion of the intermediate component being positioned between the spaced legs, the intermediate component being connected at a central portion thereof to the spaced legs of the lower component by a pin and being rotatable about the pin, and pivot means operatively associated with the intermediate component and lower component to cause the intermediate component to rotate about the pin.

14. The adjustable connector of claim 13 wherein the pivot means includes a screw carried by the lower component and secured against lateral shifting relative to the lower component, the intermediate component threadibly accommodating the screw at one end of the intermediate component such that as said screw is rotated, the one end of the intermediate component travels along the screw to rotate the intermediate component about the pin.

15. The adjustable connector of claim 14 including at least one set screw carried by the lower component for engaging the intermediate component to prevent further rotation of the intermediate component relative to the lower component.

* * * * *